(12) United States Patent
Squires et al.

(10) Patent No.: US 10,107,731 B2
(45) Date of Patent: Oct. 23, 2018

(54) MATERIAL TESTING APPARATUS AND METHOD

(71) Applicant: ILLINOIS TOOL WORKS INC., Glenview, WI (US)

(72) Inventors: Steven R. Squires, Marlow (GB); Benjamin P. Jeppesen, High Wycombe (GB); Andrew J. Smith, St. Albans (GB)

(73) Assignee: ILLINOIS TOOL WORKS INC., Glenview, IL (US)

( * ) Notice: Subject to any disclaimer, the term of this patent is extended or adjusted under 35 U.S.C. 154(b) by 650 days.

(21) Appl. No.: 14/367,589

(22) PCT Filed: Dec. 14, 2012

(86) PCT No.: PCT/US2012/069711
§ 371 (c)(1),
(2) Date: Jun. 20, 2014

(87) PCT Pub. No.: WO2013/096111
PCT Pub. Date: Jun. 27, 2013

(65) Prior Publication Data
US 2014/0331780 A1   Nov. 13, 2014

(30) Foreign Application Priority Data
Dec. 21, 2011 (GB) .................................. 1122111.6

(51) Int. Cl.
*G01N 3/08* (2006.01)
*G01N 3/32* (2006.01)
*G01K 13/00* (2006.01)

(52) U.S. Cl.
CPC ............... *G01N 3/32* (2013.01); *G01K 13/00* (2013.01)

(58) Field of Classification Search
CPC . G01N 3/32; G01N 25/72; G01N 3/08; G01L 13/00; G01L 1/24; G01K 13/00
(Continued)

(56) References Cited

U.S. PATENT DOCUMENTS 4,378,701 A * 4/1983 Mountain .............. G01N 25/72
                                                              374/121
5,201,582 A * 4/1993 Lesniak ................. G01N 25/72
                                                              250/332
(Continued)

FOREIGN PATENT DOCUMENTS

CN        101688824 A     3/2010
GB           214737 A     4/1924
(Continued)

OTHER PUBLICATIONS

V. Bellenger et al., "Thermal and mechanical fatigue of a PA66/glass fibers composite material," International Journal of Fatigue, 28, 2006, pp. 1348-1352.
(Continued)

*Primary Examiner* — Jonathan Dunlap
*Assistant Examiner* — Octavia Hollington
(74) *Attorney, Agent, or Firm* — McCarter & English, LLP (57) ABSTRACT

A method of operating a material testing apparatus comprises conducting a test by applying a fluctuating load to a material specimen at a variable test frequency, measuring the temperature of the specimen during application of the load, and varying the test frequency on the basis of the measured temperature whereby to prevent the specimen from exceeding a predetermined maximum temperature during the test. A corresponding material testing apparatus is also provided.

35 Claims, 3 Drawing Sheets

(58) Field of Classification Search
USPC .................................................. 73/805, 808
See application file for complete search history.

(56) References Cited

U.S. PATENT DOCUMENTS

| | | | |
|---|---|---|---|
| 5,712,431 | A | 1/1998 | Vilendrer |
| 6,023,980 | A | 2/2000 | Owen et al. |
| 8,393,216 | B2* | 3/2013 | Guy .................... G01M 5/0016 73/577 |
| 9,243,985 | B2* | 1/2016 | Khonsari ................ C22C 38/00 |
| 2002/0170361 | A1 | 11/2002 | Vilendrer et al. |
| 2008/0011091 | A1* | 1/2008 | Weldon, Jr. ............. G01L 1/255 73/766 |
| 2009/0048788 | A1 | 2/2009 | Darehbidi et al. |
| 2010/0175480 | A1 | 7/2010 | Guy |
| 2011/0249115 | A1* | 10/2011 | Genest ................... G01N 25/72 348/125 |
| 2011/0288791 | A1* | 11/2011 | Jeppesen ................. G01N 3/38 702/42 |

FOREIGN PATENT DOCUMENTS

| | | |
|---|---|---|
| KR | 101041899 B1 | 6/2011 |
| RU | 1826029 A1 | 7/1993 |

OTHER PUBLICATIONS

ISR for PCT/US2012/069711 mailed May 2, 2013.
GB Search Report for GB1122111.6 dated Apr. 18, 2012.

* cited by examiner

MATERIAL TESTING APPARATUS AND METHOD

RELATED APPLICATIONS

The present application is a National Phase of International Application Number PCT/US2012/069711 filed Dec. 14, 2012 and claims priority of British Application Number 1122111.6 filed Dec. 21, 2011.

The present invention relates to a materials testing machine and a method of operating a materials testing machine, and in particular to the field of fatigue testing and the control of autogenous specimen heating during testing.

Materials testing machines are used for testing the physical characteristics of material specimens or components. Fatigue testing involves determining the behaviour of materials under fluctuating loads. Typically, a specified mean load (which may be zero) and an alternating load are applied to a specimen and the number of cycles required to produce failure (fatigue life) is recorded. Loads may be applied for example axially, in torsion, in flexure, shear, friction, or any combination of these.

In the process of mechanically testing specimens and samples of material, energy is imparted into the specimen by the mechanical forces and deformations applied during the test. A proportion of this energy manifests itself as autogenous heating of the specimen. In a cyclic fatigue test, the forces and deformations are applied in a repetitive manner and the energy absorption rate is generally proportional to the test frequency (i.e. the faster the test frequency, the hotter the specimen will become).

At higher test frequencies, the self-heating effect on the specimen can lead to a significant temperature rise. This is the case in any cyclic loading test, including complex cyclic loading or tests using pseudo-random spectral waveforms, whether the specimen is loaded in tension or torsion, etc.

Whilst for metal specimens such fatigue testing can generally be carried out at relatively high test frequencies, for some specimen material types, e.g. plastics and composites, the self-heating effect of fatigue testing can cause the specimen temperature to exceed predetermined test limits (e.g. the resin in the composite may exceed its working temperature), which can reduce the validity of the test results.

To counter this, the operator conducting a fatigue test commonly sets the test frequency to a conservative value for which it is thought that the working temperature will not be exceeded during the test. Testing standards (e.g. ISO standards, or standards set by manufacturers or customers) may either specify a maximum temperature which may not be exceeded, or a maximum permitted temperature rise during the test, and the operator is required to limit the fatigue test frequency so that the autogenous heating does not cause this limit to be exceeded. As a result, a conservative test frequency is used which unnecessarily extends the duration of the test, reduces the throughput of tests on the machine and increases the cost per test. In some cases, a testing standard may simply specify a maximum test frequency as a simple and excessively cautious way of preventing the specimen from overheating. Examples of relevant standards are EN ISO 13003, ASTM D3479/D3479M "Standard Test Method for Tension-Tension Fatigue of Polymer Matrix Composite Materials" and ASTM D7615/7615M "Standard Practice for Open-Hole Fatigue Response of Polymer Matrix Composite Laminates".

Many different material testing systems are known in the prior art, including testing systems designed for testing specimens at high or low temperatures. GB 214,737 discloses a method and device for testing materials specimens, in which the specimen is held in a liquid chamber during the test, and the specimen temperature is kept constant by adjusting the flow of liquid through the chamber.

US2002/0170361 A1 discloses a device for testing the response of a material to a repetitive shear force, in which the material specimen is positioned in an environmental control chamber having heating and cooling elements, and the chamber can be set to a desired temperature and retained at a constant temperature throughout the test using a PID control system.

However, these systems rely on controlling the temperature of the environment surrounding the test specimen, which increases the complexity of the apparatus. Furthermore, such forced cooling, which may also be achieved by introducing cooler air or using fans, can only be used to limit specimen heating if the relevant test standard permits it. This is not always the case, since forced cooling changes the test environment and certain test standards specify test conditions without such cooling. In addition, forced cooling creates larger temperature gradients across the specimen, making it more difficult to estimate the true specimen temperature. It would therefore be desirable to provide a testing apparatus and method by means of which it is possible to minimise testing times and maximise throughput, without the specimen temperature exceeding a particular temperature limit, by controlling autogenous heating of the specimen without needing to control the temperature of the environment surrounding the specimen.

The present invention provides a method and apparatus whereby the test frequency can be automatically adjusted so as reduce the test time whilst maintaining a specified cyclic load or stress, but without exceeding a specified specimen working temperature. Preferably, the invention is arranged such that the test is conducted in the shortest possible time, i.e. the test frequency is actively controlled to minimise the test time.

In particular, the present invention provides method of operating a material testing apparatus, as claimed in claim 1. In accordance with the invention, the method comprises conducting a test by applying a fluctuating load to a material specimen at a variable test frequency, measuring the temperature of the specimen during application of the load, and varying the test frequency on the basis of the measured temperature so as to prevent the specimen from exceeding a predetermined maximum temperature during the test. The test is typically continued until failure of the specimen occurs, or a specified number of loading cycles have been carried out. Preferably, the test frequency is varied in such a way as to minimise the time taken for the test to be completed, without the specimen exceeding the maximum temperature during the test.

Preferably, the method comprises using a feedback control loop and supplying the measured specimen temperature to a controller which controls the test frequency based on the measured specimen temperature. The test frequency may be varied during the test (i.e. during application of the load) by using proportional-integral control of the test frequency on the basis of the measured specimen temperature, or by using proportional-integral-derivative control or other related types of control. In this way, the frequency can be maximised during the test such that specimen temperature closely tracks a target temperature, without exceeding any given temperature limit.

Although the required control loop parameters may be selectable by the operator, in one embodiment the invention provides automatic adaptive tuning of the control loop in order to minimise operator input, and maximise the effectiveness of the control parameters.

By using an effective control system to control the test frequency in response to the specimen temperature, the test time is greatly reduced by keeping the average temperature closer to an ideal target temperature, and significant swings in temperature are avoided, which might otherwise exacerbate material fatigue.

In another aspect, the invention provides a material testing apparatus comprising an actuator for applying a fluctuating load to a material specimen at a variable test frequency, means for measuring the temperature of the specimen during application of the load, and means for varying the test frequency on the basis of the measured temperature so as to prevent the specimen from exceeding a predetermined maximum temperature during the test.

Embodiments of the invention will now be described, by way of example, with reference to the accompanying drawings, in which.

In a conventional material testing machine, an actuator applies a load to a specimen, based on specified test parameters, or commanded variables, such as displacement, load or strain. In a fatigue test, a fluctuating load is applied to the specimen at a specified test frequency. The required test frequency is input to a waveform generator, which generates the required control signal for driving the actuator in accordance with a commanded variable. In order that the load actually applied to the specimen closely follows the desired loading pattern, feedback control is typically used to minimise the error between the commanded variable and a measured value, and the error is provided to a controller which drives the actuator.

In a typical fatigue test, the operator will set the test frequency to a suitable value, based either on a specified testing standard or a value which is known to be sufficiently low so as not to cause the specimen to overheat during the test. In either case, the test frequency is typically set to a conservative value, particularly when testing composite materials, since the results of the test will be compromised if the specimen temperature exceeds the working limit for the material.

The present invention aims to increase the throughput in the testing apparatus without exceeding the specified working temperature of a specimen, by monitoring the temperature of the specimen during testing and controlling the frequency of the cyclic loading of the specimen in such a way that the specimen temperature remains within acceptable limits. In other words, the temperature of the specimen is controlled by adjusting the test frequency.

Figure 1:
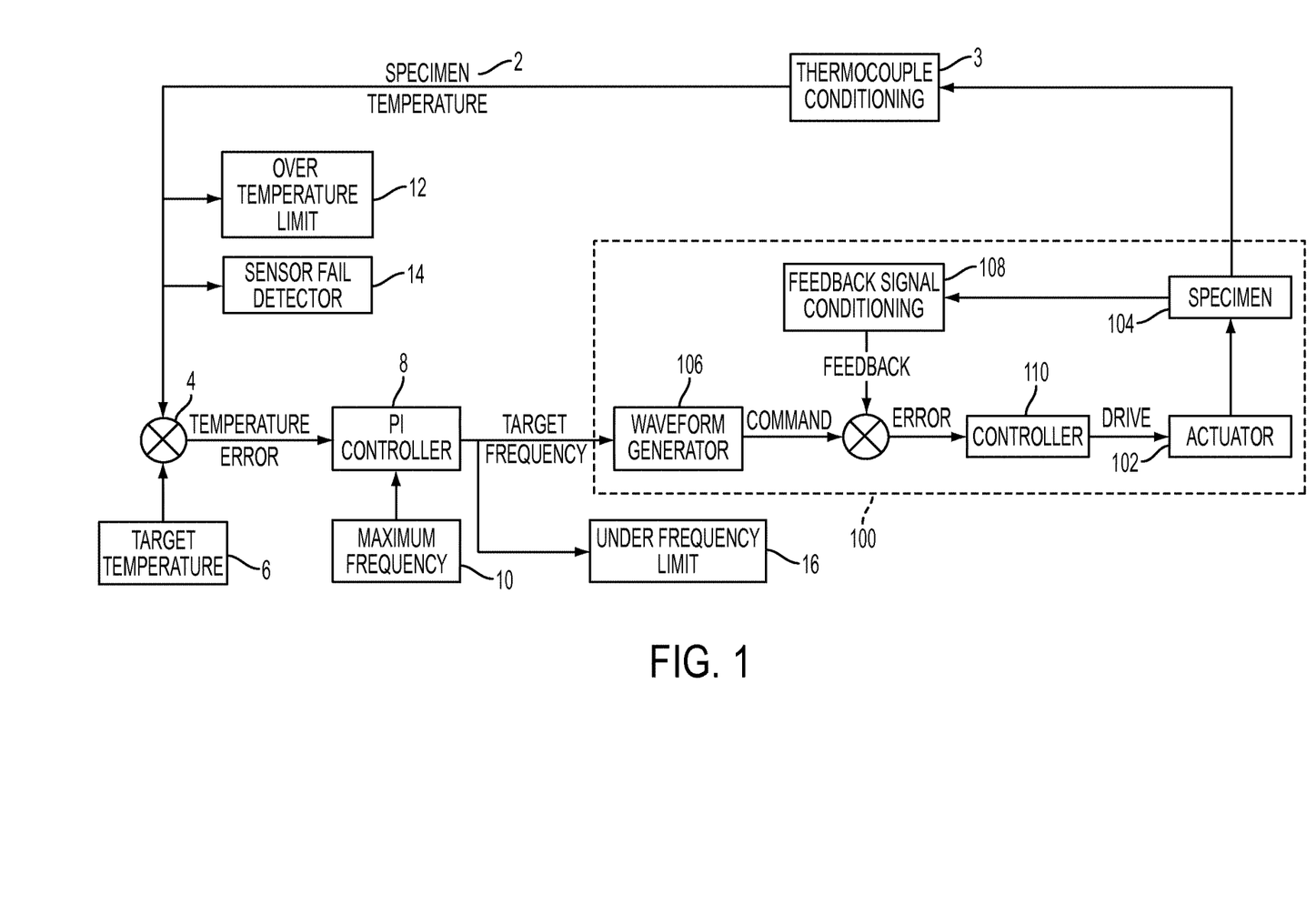
FIG. 1 shows schematically a material testing system for implementing the method in accordance with a first embodiment of the invention, with fixed tuning of the feedback control.

FIG. 1 illustrates a testing apparatus according to an embodiment of the invention, including a control system for adjusting the test frequency in response to the detected temperature of the specimen. In this embodiment, the apparatus includes components of a conventional fatigue testing system, including an actuator 102 for applying a cyclic load to a specimen 104 in accordance with a command signal generated by a waveform generator 106, which has a desired test frequency as an input. As described above, the actual force applied to the specimen is measured and fed back, via suitable signal conditioning 108, in a control loop, and the difference between the commanded value and the measured value is supplied to a controller 110 which generates the drive signal for the actuator. These conventional features are generally shown within the dotted line 100. In one example, the controller 110 is a proportional, integral, derivative and lag (PIDL) controller, although other controllers may be used. It will be appreciated that the fatigue test may be run using position as a control parameter, rather than load. In that case the position is measured and fed back to the controller 110, via any required position signal conditioning.

In order to control the temperature of the specimen in accordance with the invention, the apparatus includes an outer-loop control system comprising means for measuring the specimen temperature 2, means 4 for comparing the measured temperature with a target temperature 6 to produce a temperature error value, and a controller 8 for receiving the temperature error value, determining a required test frequency on the basis of the temperature error, and providing an output to the waveform generator 106 to adjust the test frequency accordingly. One of the benefits of providing the temperature control function as an outer-loop control system is that it can be retrofitted to existing testing systems which may correspond to the features designated 100.

The apparatus may provide the operator with the ability to input a maximum specimen temperature and/or a maximum test frequency 10, or alternatively such parameters may be generated or input to the system other than by the operator. These maximum values are typically used to ensure that the test does not exceed suitable operating limits. If the specimen reaches the specified maximum temperature, this generally indicates that the control is not functioning adequately, and the test should stop. The maximum frequency is typically a specified maximum operating limit of the testing machine, and the test can continue indefinitely at this frequency. As an alternative to the maximum frequency, it may be preferable to specify a maximum strain rate, from which the maximum test frequency can be automatically derived.

The operation of the temperature control system will now be described with reference to FIG. 1. The controller 8 shown in FIG. 1 consists of a known type of proportional and integral (PI) controller, which operates on the following variables:

the Process Variable (PV) is the specimen temperature
the Manipulated Variable (MV) is the test frequency
the Set Point (SP) is the target specimen temperature
Error (e)=SP−PV In other embodiments, the controller may be a proportional-integral-derivative (PID) controller, or may use other combinations of proportional, integral and derivative control, such as a PD, P or I controller. Any such controllers may be used in any of the embodiments described below, with appropriate modifications which will be apparent to the skilled person.

In the illustrated embodiment, the PI controller is in the form of:

$$MV(t)=K_P e(t)+\int_n^t K_I e(\tau)d\tau,$$

where $K_P$ is the proportional gain, and $K_I$ is the integral gain.

In the arrangement described above, the PI control is modified from standard form so that the integrator is in terms of test frequency (i.e. $K_I e$ is integrated). This allows for a straightforward initialisation of the system, by using the test start frequency as the initial integrator value at the start of the test.

In the embodiment of FIG. 1 the proportional gain $K_P$ and the integral gain $K_I$ may be set by the operator, by means of suitable inputs to the controller 8 (not shown).

The difference between the measured specimen temperature and the input target temperature is determined as the temperature error value, which is then provided as an input to the PI controller 8. The target temperature may be input directly by the operator, or may be determined by other suitable means. For example, the target temperature may be derived from the maximum temperature in such a way as to ensure that the specimen temperature does not exceed the maximum temperature during the test. The PI controller implements the feedback control in the form set out above and interfaces with the conventional testing system 100 by sending the generated test frequency signal to the waveform generator 106.

In the embodiment of FIG. 1, the specimen temperature is measured using a thermocouple, and fed back via any required conditioning 3 of the thermocouple signal into the outer control loop. Such conditioning may be carried out by known electronic modules. Typically, the thermocouple is bonded to the specimen surface, although one or more thermocouples may be embedded into the specimen, or otherwise integrally formed within it. Other temperature measurement arrangements may be used as alternatives, or in addition to the use of thermocouples, for example infrared detectors, pyrometers or a thermal imaging camera. The temperature measurement may be obtained using multiple sensors, which may located in or on different parts of the specimen, and the temperature measurement used in the control loop may be obtained in various different ways from the multiple measurements. For example, the multiple measurements may be averaged, or the maximum of the individual measurements may be used. For example, a thermal imaging camera or other means may allow the peak specimen temperature to be identified and controlled. In this way, the temperature distribution can be measured all over the specimen, and not just at a single point, and the detected peak temperature could be used to control the test, wherever it might occur on the specimen. Furthermore, it is envisaged that the specimen temperature may be determined in any way which may be specified in any relevant testing standards.

In operation of the illustrated embodiment of the system, the test specimen is located by the operator in the testing machine, and the operator sets the proportional and integral gains, or these can be set to default values. The gains are typically fixed for the duration of the test, although in some implementations they may be adjusted by the operator during the test. The operator may also set a maximum specimen temperature and/or a maximum test frequency.

Where the temperature measurement is carried out by means of a measurement system integrated in or attached to the specimen, this is appropriately connected to the testing machine prior to beginning the test.

The test is commenced in a conventional manner, and a specified loading profile is applied to the specimen. By means of the outer feedback loop shown in FIG. 1, the specimen temperature is measured and compared with a target temperature to produce a temperature error, which is provided to the PI controller 8. The PI controller uses the temperature error to produce a test frequency signal which is provided to the waveform generator 106, and the test frequency is thereby adjusted to control the specimen temperature. Accordingly, the test frequency can be maximised in order to minimise the test time and maximise throughput, without the specimen exceeding its working temperature, or any other specified maximum temperature.

Different control profiles (i.e. test frequency profiles) may be employed to reduce the test time in a particularly effective way, depending on the control gains and the initial test frequency. For example, the maximum frequency could be selected as the initial frequency at the start of the test, in order to raise the specimen temperature to near the target as quickly as possible. By selecting strong control gains, the frequency would be reduced quickly as soon as the target temperature is reached. However, this approach would produce some overshoot of the controlled temperature, which would in turn require a more conservative target temperature to be set in order to avoid overheating the specimen. Therefore, when conducting long-term tests, an alternative approach is to start the test at a frequency below the expected long-term frequency value, thereby allowing the target temperature to be less conservative and further reducing the test time over the course of a long-term test.

Additional limit mechanisms may be provided, as shown in FIG. 1, in order to pause the test under certain circumstances. In particular, the system may be arranged to detect the measured specimen temperature exceeding a specified maximum value, as indicated by the 'over temperature limit' detection 12. Additional detection of a temperature sensor failure may be provided, as indicated by the 'sensor fail detector' 14. The failure of a sensor may result from a fault in the sensor itself, or from the detachment of the sensor from the specimen or from some other failure in the feedback of the temperature measurement to the PI controller. Such failure may be detected by monitoring the specimen temperature signal and detecting a break in the temperature feedback (which may indicate complete sensor failure or a connection failure), or a sudden drop in the measured temperature (which may indicate detachment of a thermocouple from the specimen, for example). Other error detection may be provided, for example to detect control errors such as the target test frequency output from the PI controller 8 being too high or too low. Such control errors can be detected by monitoring the relevant control signals and comparing them with specified thresholds, as indicated by the 'under frequency limit' detection 16 in FIG. 1. Any of the specified limit mechanisms may be arranged to stop or pause the test when problems are detected, or to provide an appropriate corrective action.

Figure 2:
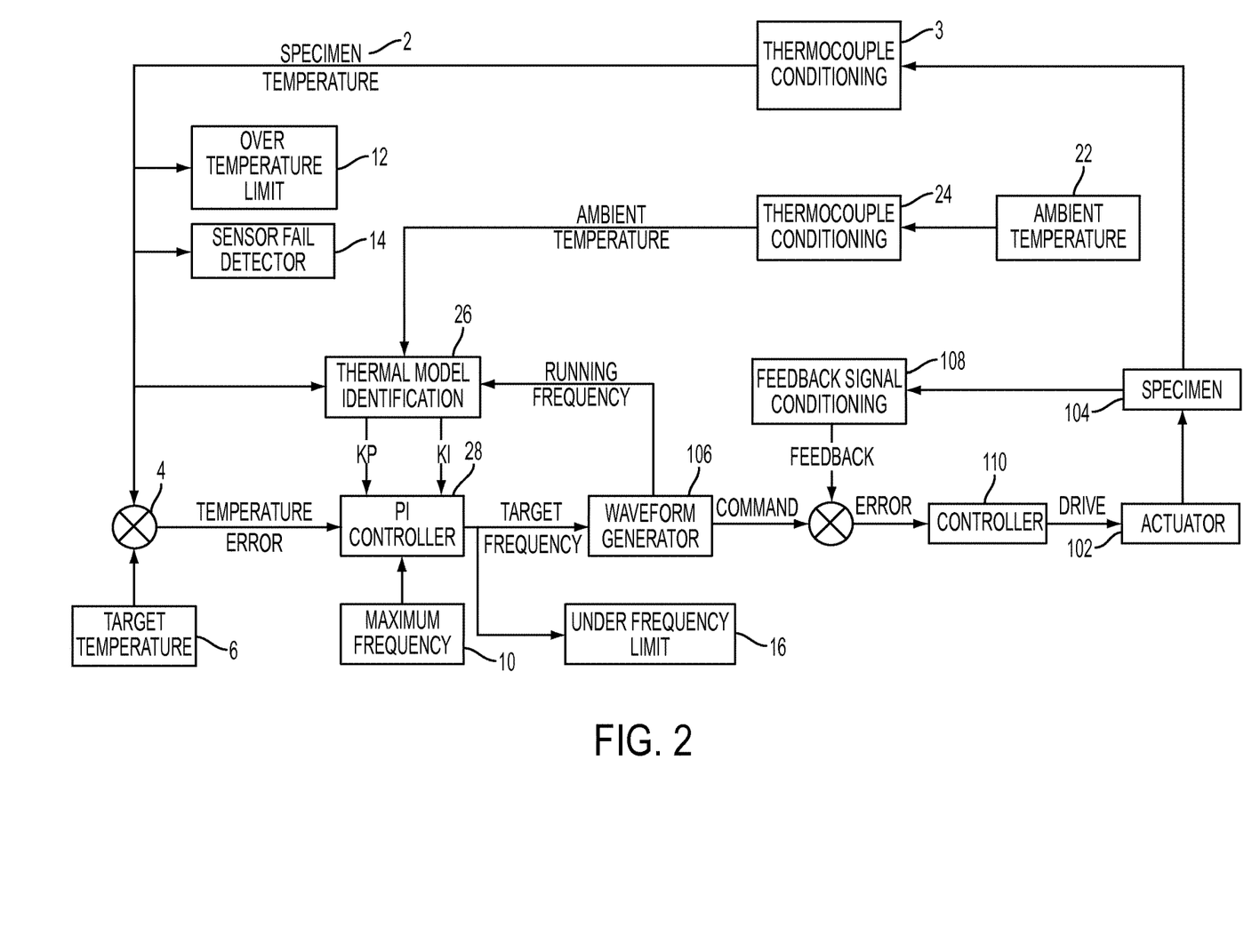
FIG. 2 shows schematically a material testing system in accordance with a further embodiment of the invention, including adaptive tuning of the feedback control gains with measured ambient temperature.

FIG. 2 illustrates a further embodiment of a temperature controlled testing system, in which tuning of the outer loop temperature control is carried out automatically. Preferably, this embodiment provides fully automatic, adaptive tuning of the outer temperature control loop. The main components of the testing system are the same as those shown in FIG. 1, and like components are given the same reference numerals. The main difference in the system of FIG. 2 is the provision of a thermal model identification module 26 for calculating the proportional and integral gains used by the PI controller 28. The gains are determined by the thermal model identification module on the basis of various inputs from the system, namely the measured specimen temperature 2, the running frequency (i.e. commanded test frequency) provided by the waveform generator 106, and preferably a measured ambient temperature. The ambient temperature 22 may be determined and provided to the thermal model identification module 26 by any suitable measurement means, such as a thermocouple, via any necessary signal conditioning 24. It is desirable to condition all signals used by the thermal parameter identification (specifically the specimen and ambient temperatures, rate of change of specimen temperature and the test frequency) with the same filter dynamics in order not to reduce the effectiveness of the identification process by introducing additional dynamics. For example, if the specimen temperature signal is low-pass filtered, then the same low-pass filtering should preferably be applied to the ambient temperature, rate of change of specimen temperature and test frequency as used by the identification algorithm.

Figure 3:
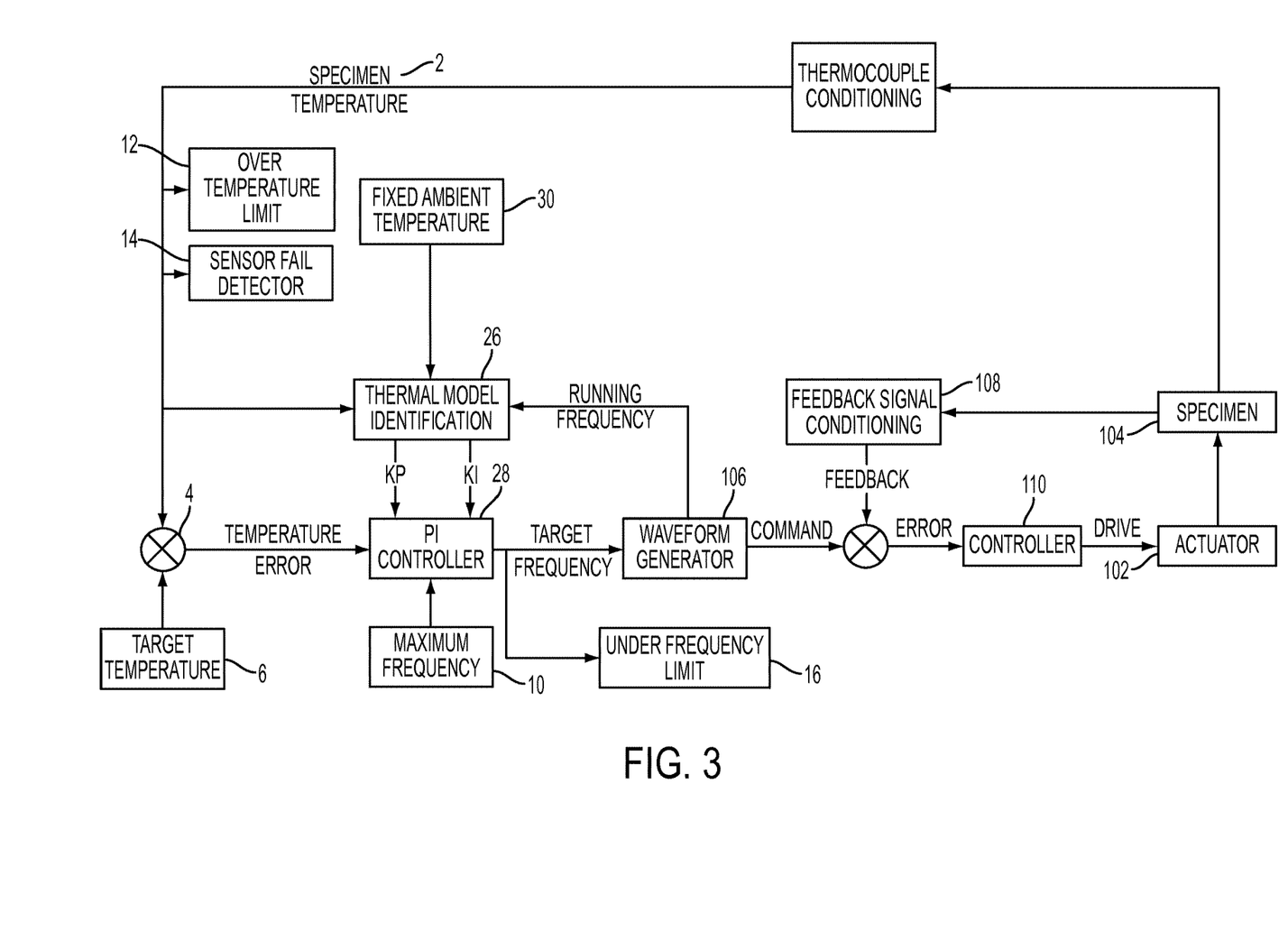
FIG. 3 shows schematically an embodiment including adaptive tuning of the feedback control gains in accordance with an alternative arrangement, using an assumed (fixed) ambient temperature.

As an alternative to the measurement of ambient temperature as shown in FIG. 2, the ambient temperature used by the thermal model identification module may be input as a fixed value. The ambient temperature value may be entered by the operator, or derived from another source. This arrangement may be appropriate in circumstances where the ambient temperature is constant and known, and the need for active ambient temperature measurement is therefore eliminated. For example, the testing apparatus may be used in a temperature controlled environment, in which case the operator can enter the known temperature, or alternatively the temperature could be provided to the testing apparatus as an output from the system controlling the temperature of the controlled environment. FIG. 3 shows an arrangement similar to that of FIG. 2, including the thermal model identification module 26, but in this embodiment the module is provided with a fixed ambient temperature 30 as an input, instead of the measured ambient temperature in the embodiment of FIG. 2.

In an alternative embodiment (not shown), a measured ambient temperature may be used as an input to the feedback controller governing the test frequency, even where there is no adaptive tuning of the feedback parameters. For example, preset or operator controlled feedback gains may be used in the control of the test frequency, as in FIG. 1, but the set point for the feedback control may be the difference between the specimen temperature and ambient temperature, rather than the specimen temperature itself. In this case, the measured ambient temperature, or otherwise an assumed ambient temperature value, would be used as an input.

In both systems of FIGS. 2 and 3, the gains calculated by the thermal model identification module 26 are then output to the PI controller 28. Where a different type of controller is used in place of a PI controller (e.g. a PID controller), the required gains are calculated accordingly.

Using the illustrated PI controller 28, the thermal model identification module 26 is designed to determine ideal values of the proportional and integral gains and eliminate the need for the operator to adjust the gains manually, thereby enabling more effective control of the specimen temperature and further improved testing throughput. This is achieved by calculating the gains using a thermal model as set out in detail below, although other thermal models may be used to achieve a similar result. The described thermal model allows the gains to be calculated effectively on the basis of the specimen temperature, ambient temperature and test frequency.

Once the thermal parameters of a specimen and appropriate control gains have been estimated during a test, they will be applicable to other tests with physically similar specimens. In fact, it would enable more accurate frequency control and hence a faster test for following tests with similar specimens if the appropriate thermal parameters or control gains are set as fixed values at the beginning of each following test. For convenience and better physical understanding, the user may prefer to note and reuse thermal parameter values rather than controller gains when setting up a following test. Therefore, the control system may give the option to use fixed control tuning or adaptive (automatically estimated) control tuning; if the control tuning is fixed, the user may be given a further choice to specify controller gains directly or the thermal parameter values that determine them In the present embodiment, a simple thermal model is used, which is an ordinary differential equation predicting the rate of change of specimen temperature given the test frequency and difference between specimen and ambient temperatures:

$$\frac{d\theta_s}{dt} = c_F F - c_L(\theta_s - \theta_a), \quad (1)$$

where $\frac{d\theta_s}{dt}$ = rate of change of specimen temperature [° C./s]

$c_F$ = heating coefficient [° C./(s Hz)]

$c_L$ = cooling coefficient [1/s]

$F$ = test frequency [Hz]

$\theta_s$ = specimen temperature [° C.]

$\theta_a$ = ambient temperature [° C.]

The model results from considering the energy flows into the specimen, assuming that each test cycle introduces the same amount of energy into the specimen, and that the rate of energy lost due to cooling is proportional to the difference between the specimen and ambient temperatures.

Note that the dynamic load applied to the specimen in each cycle must remain constant, otherwise $c_F$ will vary.

Identification Equations

The thermal model of equation (1) can be rewritten as a simple linear algebraic equation:

$$v = c_F F - c_L \delta \quad (2)$$

$$v = (c_F \quad -c_L)\begin{pmatrix} F \\ \delta \end{pmatrix},$$

where $v = \frac{d\theta_s}{dt}$ and $\delta = \theta_s - \theta_a$

By writing the equation like this, standard parameter identification techniques (see for example the book Adaptive Control, Second Edition, by Karl J. Åström and Björn Wittenmark) can be used to estimate $c_F$ and $c_L$. The standard form of equation is:

$$y = C^T x + \varepsilon_y \quad (3),$$

where y are noisy measurements composed of errors $\varepsilon_y$ and the correct values calculated from $C^T x$. C is a matrix of parameters to be identified, and x are 'known' inputs that are considered to be without error. If a whole series of values $X = [x_1 \ x_2 \ \ldots \ x_n]^T$ and $Y = [y_1 \ y_2 \ \ldots \ y_n]^T$ are available, the 'least squares' best estimate of C is:

$$\hat{C} = (X^T X)^{-1} X^T Y = PQ \quad (4)$$

where $P = (X^T X)^{-1}$ and $Q = X^T Y$.

When applied to online estimation for 'adaptive' control, these equations are often converted to 'recursive' form with a 'forgetting factor', which governs how quickly old data is 'forgotten' in favour of new data. Since old data is eventually forgotten, there must be frequent changes in the measured variables for accuracy to be maintained, otherwise estimates will start to 'drift'. In this application however, the parameters are expected to be constant and the most significant changes in measurements are expected to be at the beginning of the test, so equation (4) is applied directly using the following procedure:

By comparing equation (3) to equation (2), it can be seen that:

$$y = v = \frac{d\theta_s}{dt}, C = \begin{pmatrix} c_F \\ -c_L \end{pmatrix} \text{ and} \quad (5)$$

$$\underline{x} = \begin{pmatrix} F \\ \delta \end{pmatrix} = \begin{pmatrix} F \\ \theta_s - \theta_a \end{pmatrix}$$

On each update of the thermal parameter identification process, the matrices Pinv (used initially for convenience instead of P), Q from equation (4) and the parameter estimates are updated as follows:

$$invP_k = invP_{k-1} + \begin{pmatrix} F_k^2 & F_k \delta_k \\ F_k \delta_k & \delta_k^2 \end{pmatrix} \quad (6)$$

$$Q_k = Q_{k-1} + \begin{pmatrix} F_{k-1} v_k \\ \delta_{k-1} v_k \end{pmatrix}$$

$$\tilde{C}_k = (Pinv_k)^{-1} Q_k$$

These equations are typically only updated when certain conditions are met, which may include:
- The temperatures have changed by a specified minimum amount since the last update, and the magnitude of δ is sufficient (as discussed in more detail below);
- Pinv is not inverted until there have been sufficient updates for it to be numerically well-conditioned and therefore invertible.

Rules for Setting $K_P$ and $K_I$

The control equation for setting the test frequency F based on proportional gain $K_P$, integral gain $K_I$ and target temperature $\theta_t$ is (in Laplace Transform form):

$$F = \left(K_P + \frac{K_I}{s}\right)(\theta_t - \theta_s) \quad (7)$$

By converting the original thermal equation (1) to Laplace Transform form and substituting equation (7) for F into this equation, a transfer function for the thermal system including controller can be derived:

$$\theta_s = \frac{\left(1 + s\frac{K_P}{K_I}\right)\theta_t + \left(\frac{c_F}{c_L}\right)\frac{s}{K_I}\theta_a}{1 + s\left(\frac{1 + \left(\frac{c_F}{c_L}\right)K_P}{\left(\frac{c_F}{c_L}\right)K_I}\right) + \frac{s^2}{c_F K_I}} \quad (8)$$

Equation (8) shows that the error will tend to zero if the ambient temperature remains constant, and the dynamics are 'second order', with 'natural frequency' (speed of response towards zero error) $\Omega = \sqrt{K_I c_F}$ and 'damping factor':

$$\zeta = \frac{1 + \left(\frac{c_F}{c_L}\right)K_P}{\left(\frac{2}{c_L}\right)\sqrt{K_I c_F}} \quad (9)$$

By rewriting equation (9), an equation for the integral gain $K_I$ can be derived in terms of other terms:

$$K_I = \frac{c_L^2}{4\zeta^2 c_F}\left(1 + \left(\frac{c_F}{c_L}\right)K_P\right)^2 \quad (10)$$

In this implementation, the controller was designed using two design parameters n and $\zeta_{design}$. $K_P$ and $K_I$ should be chosen to achieve a damping factor $\zeta_{design}$ and give a controlled response n times faster than if $K_P$ had been zero. These rules result in the following equations for $K_P$ and $K_I$:

$$K_P = (n-1)\left(\frac{c_L}{c_F}\right) \quad (11)$$

$$K_I = \frac{n^2 c_L^2}{4\zeta_{design}^2 c_F}$$

It should be noted that many other design rules may be used to tune $K_P$ and $K_I$, as will be apparent to the skilled person.

Further modifications may be made to the determination of the control gains, in order to improve the performance of the automatic tuning.

In particular, it has been determined that temperature noise may give rise to poor thermal model identification. To reduce the effects of temperature noise on the thermal model identification, it may be desirable to perform the updates to the model only when the delta temperature (specimen–ambient) has changed by more than a specified amount.

Another difficulty may arise from the sensitivity of the system to offsets in the temperature measurements. The thermal model depends on the input δ=θs−θa, which is assumed by the parameter identification procedure to be 'error-free'. Any errors will cause bias in the identified parameter values. For small values of δ, a difference in calibration offset between θs and θa will cause a proportionally larger error in δ. To avoid this influencing the estimated values significantly, in one embodiment the estimation of the control parameters is not commenced until a specified minimum value of δ is reached. In addition, the test procedure preferably includes calibration of the measured specimen temperature to the ambient temperature.

During testing of the invention, it has been found that at the very start of the test where the frequency is constant, the measured specimen temperature tends to rise exponentially (i.e. the temperature rate is increasing). One reason for this is the time it takes for the internal heat to reach the thermocouple, where the temperature is measured by means of a thermocouple attached to the surface of the specimen. To counter this, in one arrangement the thermal model rejects values of the specimen temperature until the rate of change of temperature starts to fall.

It has also been found that shortly after the start of the test, the thermal model $c_F$ and $c_L$ errors, and hence the derived $K_P$ and $K_I$ errors, may be significant and could cause instability in the control loop. To counter this, the raw $K_P$ and $K_I$ factors may be filtered using an exponential moving average (EMA) filter before being sent to the PI controller. The EMA filters are initialised with zero at the start of the test so the filtered $K_P$ and $K_I$ values move gradually from zero toward final values ($K_P$ and $K_I$ of zero effectively mean that no change to the Test Frequency occurs). This modification results in improved stability of the specimen temperature control loop.

It will be appreciated that a different thermal model than that described above may be used to determine the proportional and integral gains for the PI controller, or the relevant control gains when using a controller other than a PI controller. In further developments of the thermal model, it is possible to use other parameters to more accurately control the test frequency. For example, when measuring the temperature of the specimen, it is possible for temperature sensors to be embedded within the specimen, but it is more usual and more straightforward for one or more sensors, such as a thermocouple, to be bonded to the specimen surface. Such sensors do not necessarily give a true indication of the temperature within the specimen, which may be significantly higher than the surface temperature. As a result, the internal temperature of the specimen may exceed the working temperature of the material while the detected surface temperature is still within the working range. Although this can be taken into account by lowering the allowable surface temperature threshold, the actual difference between the internal and surface temperatures will vary depending on the loading profile of the specimen and other factors. For example, if the test frequency is increased slowly, then the surface temperature may lag behind the internal temperature by a smaller amount than if the test is commenced at a high frequency. Therefore, simply reducing the temperature threshold of the surface temperature to account for the fact that the internal temperature may be higher could result in an excessively conservative temperature threshold being applied, which may unnecessarily increase the test time in certain circumstances.

In order to account for this effect, the thermal model may be configured to predict the internal temperature of the specimen on the basis of the surface temperature and other specimen and environmental information, e.g. the dimensions or shape of the specimen, thermal characteristics of the material, and the loading profile. More specifically, the thermal model may use one or more of: the specific heat capacity and thermal resistance of the material (note that for composite materials, thermal resistance can be different depending on the direction of conduction relative to the direction of the weave or layers); thermal resistance between the material surface and the mass of air at ambient temperature; thermal resistance between the specimen and the thermal mass of the rest of the machine; thermal resistances between the thermocouple and ambient air in one direction and the specimen surface in the other, etc. Using such additional information, the accuracy of the temperature control can be improved, resulting in reduced test time and increased throughput.

Although the invention has been described with respect to its use in conventional fatigue testing, various modifications are possible, and the principle of the invention may be applied in other applications to achieve the same advantages. In particular, the invention may be applied in any materials testing arrangement in which a fluctuating load is applied to a material with a controllable test frequency, including rotating bend fatigue tests, and multi-axis fatigue testing (e.g. cruciform testing). In a rotating bend fatigue test, a specimen is rotated and additionally loaded with a bending force perpendicular to the axis of rotation. The fluctuating load is therefore supplied by the rotation of the bent specimen, which provides a rapid tensile-compression loading particularly at the specimen surface, and the test frequency therefore depends on the rotation speed. The specimen temperature can therefore be controlled by adjusting the speed of rotation.

The invention claimed is:

1. Method of operating a material testing apparatus, comprising:
    conducting a test by applying a fluctuating load to a material specimen at a variable test frequency,
    measuring a temperature of the specimen during application of the load, and
    varying the test frequency on a basis of the measured temperature whereby to prevent the specimen from exceeding a predetermined maximum temperature during the test.

2. The method of claim 1, wherein
    measuring a temperature results in a measured specimen temperature,
    the method further comprising comparing the measured specimen temperature with a specified target temperature to determine a temperature error, and
    controlling the test frequency based on the determined temperature error.

3. The method of claim 2, further comprising specifying test frequency control gains before the test is commenced.

4. The method of claim 3, wherein the control gains are calculated on the basis of a thermal model of the specimen, using model parameters specified by a user before the test is commenced.

5. The method of claim 4, wherein measuring the temperature of the specimen is executed at a surface of the specimen, and an thermal model estimates the internal temperature of the specimen on a basis of the measured specimen temperature at the surface of the specimen and thermal parameters of the specimen.

6. The method of claim 3, wherein the control gains comprise proportional and integral control gains.

7. The method of claim 2, further comprising providing adaptive tuning of the test frequency control by continually calculating test frequency control gains during the test.

8. The method of claim 7, wherein the control gains are calculated on the basis of a thermal model of the specimen, using model parameters estimated during the test.

9. The method of claim 8, wherein the control gains are calculated on the basis of heating and cooling coefficients of the specimen.

10. The method of claim 9, wherein the rate of heating is proportional to the heating coefficient and to the test frequency, and the rate of cooling is proportional to the cooling coefficient and to a difference between the measured specimen temperature and an ambient temperature.

11. The method of claim 10, further comprising measuring the ambient temperature or determining an assumed value of the ambient temperature.

12. The method of claim 7, wherein the control gains are initialized to zero prior to the start of the test, and the calculated control gains are filtered during the test using an exponential moving average filter.

13. The method of claim 1, wherein the test frequency is varied on the basis of a measured maximum specimen temperature determined from different locations across the specimen.

14. The method of claim 1, wherein measuring a temperature results in a measured specimen temperature, the method further comprising determining a rate of change of the measured specimen temperature during the test, and varying the test frequency on a basis of the measured specimen temperature only once a decrease in the rate of change of the measured specimen temperature has been determined following a start of the test.

15. The method of claim 1, further comprising interrupting the test upon a detected error state.

16. The method of claim 15, wherein measuring a temperature results in a measured specimen temperature, wherein the measured specimen temperature is measured using a sensor which provides a temperature signal, and an error state is detected on a basis of a sudden drop in the measured specimen temperature or a break in the measured temperature signal.

17. The method of claim 1, wherein a duration of the test is determined by a specified number of loading cycles or a failure of the specimen, and the test frequency is varied during the test in such a way as to minimize a test duration, without the specimen exceeding a maximum temperature during the test.

18. Material testing apparatus comprising:
an actuator for applying a fluctuating load to a material specimen at a variable test frequency,
means for measuring a temperature of the specimen to obtain a measured specimen temperature during application of the load, and
means for varying the test frequency on a basis of the measured specimen temperature whereby to prevent the specimen from exceeding a predetermined maximum temperature during application of the load.

19. Apparatus of claim 18, further comprising a controller for providing a control signal indicative of a target test frequency for controlling the actuator, on a basis of the difference between the measured specimen temperature and a specified target temperature.

20. Apparatus of claim 19, wherein the controller is arranged to generate a target test frequency signal using predetermined control gains.

21. Apparatus of claim 20, wherein the controller is arranged to calculate the control gains on the basis of a thermal model of the specimen, using model parameters specified by a user before application of the load to the specimen.

22. Apparatus of claim 21, wherein
the means for measuring the temperature of the specimen are arranged to measure temperature at a surface of the specimen, and
the thermal model is arranged to estimate an internal temperature of the specimen on a basis of measured surface temperature and thermal parameters of the specimen.

23. Apparatus of claim 20, wherein the control gains comprise proportional and integral control gains.

24. Apparatus of claim 19, wherein the controller is arranged to continually calculate control gains for use in a generation of the target test frequency signal that results in the generated target test frequency signal, during application of the load.

25. Apparatus of claim 24, wherein the controller is arranged to calculate the control gains on the basis of a thermal model of the specimen, using model parameters estimated during the test.

26. Apparatus of claim 25, wherein the controller is arranged to calculate the control gains on the basis of heating and cooling coefficients of the specimen.

27. Apparatus of claim 26, wherein the rate of heating is proportional to the heating coefficient and to the test frequency, and the rate of cooling is proportional to a difference between the measured specimen temperature and an ambient temperature.

28. Apparatus of claim 27, further comprising means for measuring the ambient temperature or means for providing a predetermined value of the ambient temperature to the controller.

29. Apparatus of claim 24, wherein the controller is arranged to initialize the control gains to zero prior to application of the load, and to filter the calculated control gains during application of the load using an exponential moving average filter.

30. Apparatus of claim 19, wherein the controller is arranged to determine a rate of change of the measured specimen temperature during application of the load, and to vary the test frequency on the basis of the measured specimen temperature only once a decrease in the rate of change of measured specimen temperature has been determined following initial application of the load to the specimen.

31. Apparatus of claim 19, wherein the controller is arranged to interrupt application of the load in an event of a detected error state.

32. Apparatus of claim 31, comprising means for providing a signal indicative of the measured specimen temperature to the controller, wherein the controller is arranged to detect an error state on a basis of a sudden drop in the measured specimen temperature or a break in the measured temperature signal.

33. Apparatus of claim 18, wherein the test frequency varying means are arranged to vary the test frequency on the basis of a measured maximum specimen temperature determined from different locations across the specimen.

34. Control system, comprising:
comprising means for measuring a temperature of a material specimen during application of a fluctuating load; and
a controller for providing a control signal for controlling a test frequency, wherein
the control system is configured to control a material testing apparatus arranged to apply the fluctuating load to the material specimen at the variable test frequency,
the control system is configured to operate the testing material apparatus to:
conduct a test by applying the fluctuating load to the material specimen at the variable test frequency;
measure the temperature of the specimen during application of the load; and
vary the test frequency on the basis of the measured temperature whereby to
prevent the specimen from exceeding a predetermined maximum temperature during the test.

35. An assembly, comprising:
the control system of claim 34; and
the material testing apparatus, wherein
the control system is in signal communication with the material testing apparatus.

* * * * *